Figure 1:
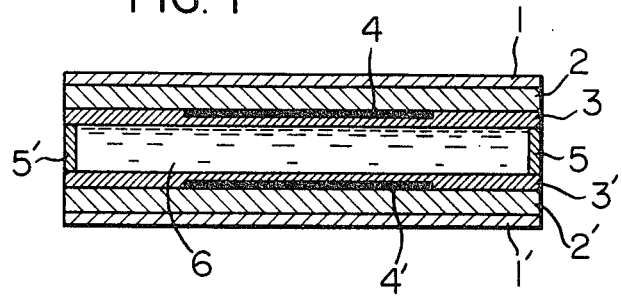

United States Patent [19]

Sato et al.

[11] 4,202,791

[45] May 13, 1980

[54] NEMATIC LIQUID CRYSTALLINE MATERIALS

[75] Inventors: Hisato Sato, Tabata; Haruyoshi Takatsu, Kodaira; Masayuki Tazume, Urawa, all of Japan

[73] Assignee: Dainippon Ink & Chemicals Inc., Tokyo, Japan

[21] Appl. No.: 11,798

[22] Filed: Feb. 14, 1979

[30] Foreign Application Priority Data

Feb. 17, 1978 [JP] Japan ................... 53-16566

[51] Int. Cl.² .......................... C09K 3/34; G02F 1/13; C07C 153/09
[52] U.S. Cl. .................................. 252/299; 252/408; 260/455 R; 350/350 R
[58] Field of Search ................... 260/455 R; 252/299, 252/408; 350/350

[56] References Cited

U.S. PATENT DOCUMENTS

| | | | |
|---|---|---|---|
| 3,876,286 | 4/1975 | Deutscher et al. | 252/299 |
| 3,923,857 | 12/1975 | Doller et al. | 252/299 |
| 3,927,064 | 12/1975 | Doller et al. | 252/299 |
| 3,947,375 | 3/1976 | Gray et al. | 252/299 |
| 3,997,536 | 12/1976 | Doller et al. | 252/299 |
| 4,002,670 | 1/1977 | Steinstrasser | 252/299 |
| 4,011,173 | 3/1977 | Steinstrasser | 252/299 |
| 4,013,582 | 3/1977 | Gaurilovic | 252/299 |
| 4,017,416 | 4/1977 | Inukai et al. | 252/299 |
| 4,053,431 | 10/1977 | Scherrer et al. | 252/299 |
| 4,062,798 | 12/1977 | Doller et al. | 252/299 |
| 4,110,243 | 8/1978 | Annick et al. | 252/299 |
| 4,118,335 | 10/1978 | Krause et al. | 252/299 |
| 4,130,502 | 12/1978 | Eidenschink et al. | 252/299 |
| 4,136,053 | 1/1979 | Steinstrasser et al. | 252/299 |
| 4,137,192 | 1/1979 | Matsufuji | 252/299 |
| 4,137,250 | 1/1979 | Reynolds et al. | 252/299 |
| 4,154,697 | 5/1979 | Eidenschink et al. | 252/299 |

FOREIGN PATENT DOCUMENTS

| | | | |
|---|---|---|---|
| 2752975 | 8/1978 | Fed. Rep. of Germany | 252/299 |
| 105701 | 5/1974 | German Democratic Rep. | 252/299 |
| 132591 | 10/1978 | German Democratic Rep. | 252/299 |

OTHER PUBLICATIONS

Krause, J., et al., Abstracts of the 6th Intern'l. Liq. Cryst. Conf., I-3, Kent, Ohio (Aug. 27, 1976).

*Primary Examiner*—Teddy S. Gron
*Attorney, Agent, or Firm*—Sherman & Shalloway

[57] ABSTRACT

Novel trans(equatorial-equatorial)1,4-disubstituted cyclohexane derivatives of the general formula

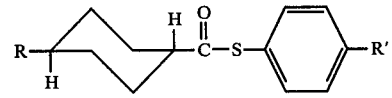

wherein R represents a linear alkyl group containing 3 to 7 carbon atoms, and R' represents a linear alkoxy group containing 2 to 5 carbon atoms or a cyano group. These compounds are nematic liquid crystals, and a composition containing at least one of these compounds is useful as an electro-optical display material.

25 Claims, 4 Drawing Figures

WEIGHT % OF $N_L$-TYPE LIQUID CRYSTAL (i) OR (ii) IN A MIXTURE OF $N_s$-TYPE LIQUID CRYSTAL MATRIX AND $N_L$-TYPE LIQUID CRYSTAL (i) OR (ii)

NEMATIC LIQUID CRYSTALLINE MATERIALS

This invention relates to novel nematic liquid crystalline compositions useful as an electro-optical display material. More specifically, this invention pertains to a trans(equatorial-equatorial) 1,4-disubstituted cyclohexane derivative expressed by the general formula

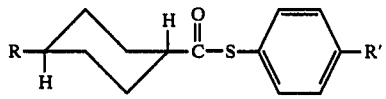 (I)

wherein R represents a linear alkyl group having 3 to 7 carbon atoms, and R' represents a linear alkoxy group having 2 to 5 carbon atoms or a cyano group; and a nematic liquid crystalline composition containing at least one such derivative.

Compounds of formula (I) have a small positive dielectric anisotropy when the substituent R' is a linear alkoxy group, and a large positive dielectric anisotropy when the substituent R' is a cyano group. (When the equation $\Delta\epsilon = \epsilon_{\|} - \epsilon_{\perp}$ is set up in which $\epsilon_{\|}$ is the dielectric constant in the director direction and $\epsilon_{\perp}$ is the dielectric contant in a direction at right angles to the director direction, compounds having $\Delta\epsilon > 0$ are considered to have a positive dielectric anisotropy, and those having $\Delta\epsilon > 0$ are considered to have a negative dielectric anisotropy.) In either case, the compounds of formula (I) are nematic liquid crystals.

Accordingly, the compounds of formula (I), either singly, or as a mixture of at least two of these compounds, or as a mixture of at least one such compound and at least one additional component (other nematic liquid crystalline and/or homologous non-liquid crystalline compounds), can be applied to field effect mode cells (to be referred to as FEM cells) suggested by M. Schadt et al., APPLIED PHYSICS LETTERS, 18, 127–128 (1971), or to dynamic scattering mode cells (to be referred to as DSM cells) suggested by G. H. Heilmeier et al., PROCEEDINGS OF THE I.E.E.E., 56, 1162–1171 (1968). The nematic liquid crystalline compositions of this invention can be especially suitably used in FEM cells which find main applications as liquid crystal display elements in pocket electronics calculators, wrist watches and other mechanical devices.

Generally, the important characteristics required of nematic liquid crystalline compounds utilized in display elements such as F.E.M. cells and D.S.M. cells include the following.

(1) They should be able to perform a white clear display.

(2) They should be chemically stable and resistant to degradation by moisture, light, etc., and have high reliability and a long service life.

(3) The nematic liquid crystal temperature should be within a broad range near room temperature, and the range of the operating temperature should be broad.

(4) They should have low viscosities and rapid response speeds. Particularly, they should have rapid speeds of response at low temperatures.

(5) They should be able to permit a free control of the operating voltage, and to be operated at low voltages. In other words, they should be able to permit a free control of the threshold voltage, and adjust it to a low value.

(6) There should be little variations in threshold voltage by temperature differences.

These requirements are very important in the commercial production of display elements of high performance. Generally, however, most of the conventional nematic liquid crystalline compounds cannot satisfy all of these requirements (1) to (6). For example, those which meet at least one of the requirements (1) and (2) are unsatisfactory in at least one of the requirements (3) to (6). Or those which satisfy at least one of the requirements (3) to (6) do not meet one of or both of the requirements (1) and (2).

The present inventors made various investigations in order to provide novel nematic liquid crystalline compounds which can meet all of these requirements (1) to (6), and found that the compounds of formula (I) can achieve this purpose. Thus, the use of these compounds can afford liquid crystal display cells which are capable of operation at low voltages and of high speed response, permit clear displays, and have a long service life.

The compound of formula (I) in accordance with this invention is produced, for example, by the following method.

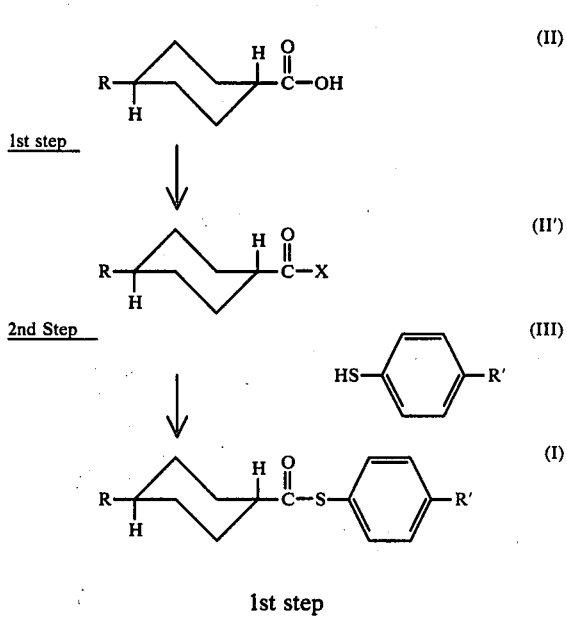

1st step

The compound of formula (II) is reacted with a halogenating agent to form the compound of formula (II') in which R is as defined above, and X is a halogen atom such as F, Cl, Br or I. In the compound of formula (II'), X is preferably a chlorine atom, and to obtain such a compound (II'), thionyl chloride may be used as the halogenating agent. The reaction is carried out at atmospheric pressure and at the reflux temperature of the reaction mixture. The compound of formula (II') needs not to be isolated from the mixture resulting from the reaction, and it is only sufficient to remove the excess of the halogenating agent.

2nd step

The crude compound of formula (II') prepared in the first step is reacted with the compound of formula (III) (in which R' is as defined hereinabove) in an inert organic solvent. Suitable inert organic solvents include diethyl ether, tetrahydrofuran, dimethylformamide and benzene. Desirably, a basic substance such as pyridine or a tertiary amine is included in the inert organic solvent to remove the hydrogen halide liberated during the reaction out of the reaction system. The reaction is carried out at a temperature of from −10° C. to room temperature under atmospheric pressure. The desired compound of formula (I) can be isolated by subjecting the reaction product to a series of purifying treatments including solvent extraction, water washing, drying, recrystallization, etc.

The starting compound of formula (III) used in the second step is produced by the following procedure.

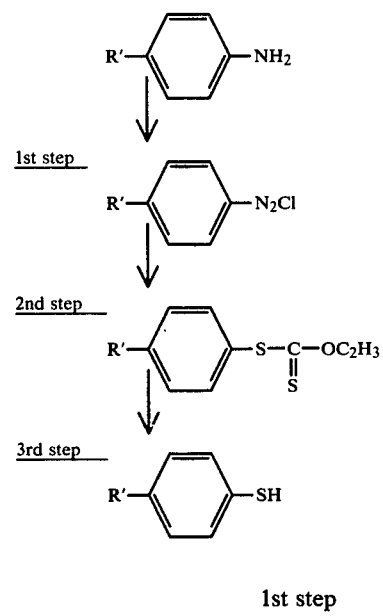

1st step

The compound of formula (a) is reacted with hydrochloric acid using water as a reaction medium, and the product is reacted further with a nitride salt at a low temperature to form the compound of formula (b).

2nd step

The mixture formed by the reaction of the first step is gradually added to a heated aqueous solution of a xanthogenate salt. The reaction product is extracted to produce the compound of formula (c).

3rd step

The compound of formula (c) produced in the second step is hydrolyzed with an alkaline solution of an alcohol, acidified, and then subjected to a series of purifying treatments including solvent extraction, water washing, drying, distillation, etc. to isolate the compound of formula (III).

The physical properties of some compounds of formula (I) produced in this manner are shown in Table 1.

Table 1

(I) structure: R—[cyclohexyl(H,H)]—CH(C(=O)—S—[phenyl]—R')

| R | R' | Transition temperature (°C.) | | | | |
|---|---|---|---|---|---|---|
| n-$C_3H_7$— | —O—$C_2H_5$ | 53 | (C⇌N), | 65 | (N⇌I) | |
| n-$C_4H_9$— | —O—$C_2H_5$ | 38 | (C⇌N), | 53 | (N⇌I) | |
| n-$C_5H_{11}$— | —O—$C_2H_5$ | 52 | (C⇌N), | 70.7 | (N⇌I) | |
| n-$C_6H_{13}$— | —O—$C_2H_5$ | 53 | (C⇌N), | 64 | (N⇌I) | |

Table 1-continued

| R | R' | Transition temperature (°C.) | | | | |
|---|---|---|---|---|---|---|
| n-$C_7H_{15}$— | —O—$C_2H_5$ | 59 | (C⇌N), | 71.5 | (N⇌I) | |
| n-$C_3H_7$— | —O-n-$C_3H_7$ | 46.5 | (C→I), | 39 | (I⇌N) | |
| n-$C_4H_9$— | —O-n-$C_3H_7$ | 41 | (C→I), | 33.5 | (I⇌N) | |
| n-$C_5H_{11}$— | —O-n-$C_3H_7$ | 48 | (C⇌N), | 50 | (N⇌I) | |
| n-$C_6H_{13}$— | —O-n-$C_3H_7$ | 48 | (C→I), | 42 | (I⇌N) | |
| n-$C_7H_{15}$— | —O-n-$C_3H_7$ | 52 | (C→I), | 50.5 | (I⇌N) | |
| n-$C_3H_7$— | —O-n-$C_4H_9$ | 49 | (C⇌N), | 53 | (N⇌I) | |
| n-$C_4H_9$— | —O-n-$C_4H_9$ | 47.5 | (C→I), | 46.5 | (I⇌N) | |
| n-$C_5H_{11}$— | —O-n-$C_4H_9$ | 57 | (C⇌N), | 61 | (N⇌I) | |
| n-$C_6H_{13}$— | —O-n-$C_4H_9$ | 53.5 | (C⇌N), | 55.5 | (N⇌I) | |
| n-$C_7H_{15}$— | —O-n-$C_4H_9$ | 60.5 | (C⇌N), | 63 | (N⇌I) | |
| n-$C_3H_7$— | —O-n-$C_5H_{11}$ | 51 | (C⇌N), | 53 | (N⇌I) | |
| n-$C_4H_9$— | —O-n-$C_5H_{11}$ | 46 | (C→I), | 41 | (I⇌N) | |
| n-$C_5H_{11}$— | —O-n-$C_5H_{11}$ | 51 | (C⇌N), | 54.5 | (N⇌I) | |
| n-$C_6H_{13}$— | —O-n-$C_5H_{11}$ | 50 | (C⇌N), | 51 | (N⇌I) | |
| n-$C_7H_{15}$— | —O-n-$C_5H_{11}$ | 55 | (C⇌N), | 57 | (N⇌I) | |
| n-$C_3H_7$— | —CN | 88 | (C→I), | 87 | (I⇌N) | |
| n-$C_4H_9$— | —CN | 83 | (C→I), | 76 | (I⇌N) | |
| n-$C_5H_{11}$— | —CN | 88 | (C⇌N), | 99 | (N⇌I) | |
| n-$C_6H_{13}$— | —CN | 91 | (C→I), | 86 | (I⇌N) | |
| n-$C_7H_{15}$— | —CN | 94 | (C⇌N), | 97 | (N⇌I) | |

In the parentheses in Table 1, C represents a crystalline phase; N, a nematic liquid crystalline phase; I, an isotropic liquid phase; and the arrow, phase transition.

The transition temperatures of the compounds shown in Table 1 were measured by observing an orthoscope image under a polarized microscope using a micro melting point measuring instrument. In the measurement of the C→N transition temperature, because the mixture exhibits a supercooled condition, it is allowed to stand at −60° C. to crystallize it, and then it is heated at a rate of 1° C. per minute, and the temperature at which the mixture shows a nematic liquid crystalline condition is taken as the C→N transition temperature.

The N⇌I temperatures and the C→N temperatures of the nametic liquid crystalline mixtures shown in the tables given hereinbelow were measured in the same manner.

As stated hereinabove, the compounds of formula (I) can be used in liquid crystalline display cells either singly, or as a mixture of at least two of these compounds, or as a mixture of at least one such compound and at least one additional component (other nematic liquid crystalline compounds and/or homologous non-liquid crystalline compounds). Above all, compositions obtained by mixing a mixture in arbitary ratios of at least two of the compounds of formula (I) as a matrix with at least one additional component selected from the group consisting of other nematic liquid crystalline compounds and homologous non-liquid crystalline compounds. The additional components that can be used as a mixture with the compound of formula (I) include (i) nematic liquid crystalline compounds having a large positive dielectric anisotropy (to be referred to as $N_p$-type liquid crystals) and homologous compounds thereof which are not liquid crystalline (to be referred to as $N_p$-type liquid crystalline homologs), (ii) nematic liquid crystalline compounds having a negative dielectric anisotropy or a small positive dielectric anisotropy (to be referred to as $N_n$-type liquid crystals) and homologous compounds thereof which are not crystalline (to be referred to as $N_n$-type liquid crystalline homologs), and (iii) mixtures of these.

Examples of preferred $N_p$-type liquid crystals and $N_p$-type liquid crystalline homologs which can be used as the additional component in the present invention are listed below.

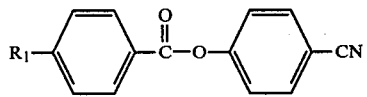

wherein $R_1$ represents $n-C_mH_{2m+1}-$, or $n-C_mH_{2m+1}-O-$ in which m is an integer of 1 to 10.

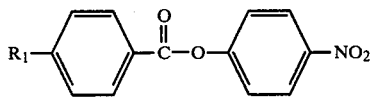

wherein $R_1$ represents $n-C_mH_{2m+1}-$, or $n-C_mH_{2m+1}-O-$ in which m is an integer of 1 to 8.

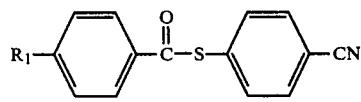

wherein $R_1$ represents $n-C_mH_{2m+1}-$ in which m is an integer of 1 to 10.

wherein $R_1$ represents $n-C_mH_{2m+1}-$, $n-C_mH_{2m+1}-O-$, or $$n-C_mH_{2m+1}-\overset{O}{\underset{\|}{C}}-O-,$$

in which m is an integer of 1 to 10.

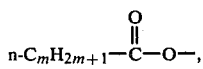

wherein $R_1$ represents $n-C_mH_{2m+1}-$ in which m is an integer of 1 to 8.

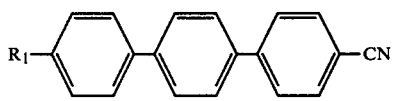

wherein $R_1$ represents $n-C_mH_{2m+1}-$ or $n-C_mH_{2m+1}-O-$ in which m is an integer of 1 to 10.

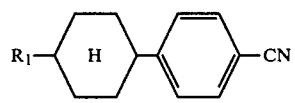

wherein $R_1$ represents $n-C_mH_{2m+1}-$ or $N-C_mH_{2m+1}-O-$ in which m is an integer of 1 to 8.

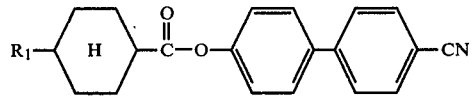

wherein $R_1$ represents $n-C_mH_{2m+1}-$ in which m is an integer of 1 to 10.

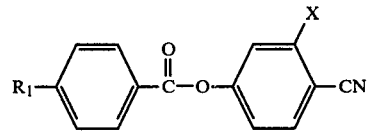

wherein $R_1$ represents $n-C_mH_{2m+1}-$ in which m is an integer of 1 to 8, and X represents F, Cl, Br or I.

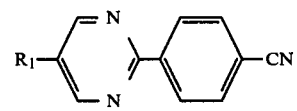

wherein $R_1$ represents $n-C_mH_{2m+1}$ in which m is an integer of 1 to 10.

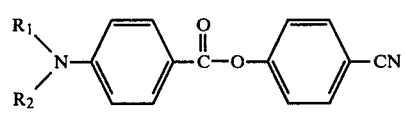

wherein each of $R_1$ and $R_2$ represents $n-C_mH_{2m+1}-$ in which m is an integer of 1 to 5.

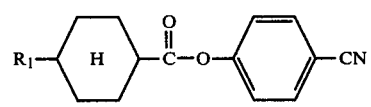

wherein $R_1$ represents $n-C_mH_{2m+1}-$ in which m is an integer of 1 to 10.

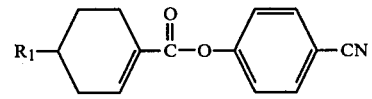

wherein $R_1$ represents $n-C_mH_{2m+1}-$ in which m is an integer of 1 to 10.

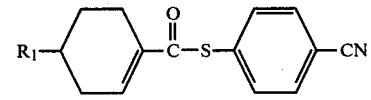

wherein $R_1$ represents $n-C_mH_{2m+1}-$ in which m is an integer of 1 to 10.

Preferred nematic liquid crystalline compositions obtainable when using these $N_p$-type liquid crystals and/or $N_p$-type liquid crystal homologs as the additional component consist of 98 to 30 mole % of the compound of formula (I) and 2 to 70 mole % of the additional component.

Preferred examples of the $N_n$-type liquid crystals and homologs thereof which can be used as the additional component in the present invention are listed below.

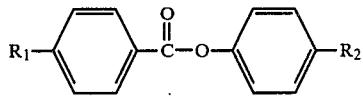

wherein $R_1$ and $R_2$ each represent n—$C_mH_{2m+1}$—, n—$C_mH_{2m+1}$—O—,

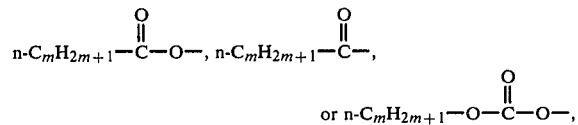

or n-$C_mH_{2m+1}$—O—$\overset{\overset{O}{\|}}{C}$—O—, in which m is an integer of 1 to 10.

wherein each of $R_1$ and $R_2$ represents n—$C_mH_{2m+1}$—, n—$C_mH_{2m+1}$—O—, or

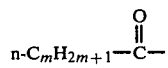

in which m is an integer of 1 to 10.

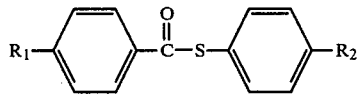

wherein each of $R_1$ and $R_2$ represent n—$C_mH_{2m+1}$ or n—$C_mH_{2m+1}$—O— in which m is an integer of 1 to 10.

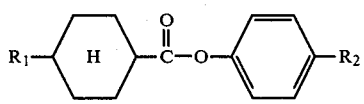

wherein $R_1$ represents n—$C_mH_{2m+1}$—, and $R_2$ represents n—$C_{m'}H_{2m'+1}$—, n—$C_{m'}H_{2m'+1}$—O— or

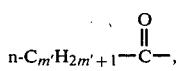

in which m and m' are integers of 1 to 10.

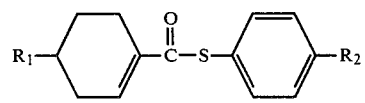

wherein $R_1$ represents n—$C_mH_{2m+1}$— and $R_2$ represents n—$C_{m'}H_{2m'+1}$— or n—$C_{m'}H_{2m'+1}$—O—, in which m and m' are integers of 1 to 10.

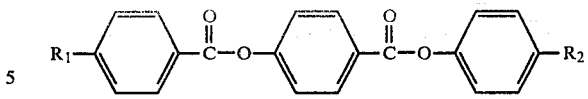

wherein $R_1$ and $R_2$ each represent n—$C_mH_{2m+1}$— or n—$C_mH_{2m+1}$—O— in which m is an integer of 1 to 6.

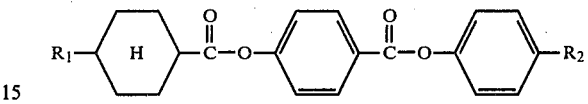

wherein $R_1$ and $R_2$ each represent n—$C_mH_{2m+1}$— or n—$C_mH_{2m+1}$—O—, in which m is an integer of 1 to 8.

Preferred nematic liquid crystalline compositions obtainable when using such $N_n$-type liquid crystals and/or homologs thereof as the additional component consist of 98 to 50 mole % of the compound of formula (I) and 2 to 50 mole % of the additional component.

The nematic liquid crystalline compositions of this invention can take some types of mixtures shown above. But since in any case, the compounds of formula (I) have very good solubility in the above-exemplified additional components, there is scarcely any restriction on the selection of the additional component to be mixed with the compound of formula (I). This bears a very important technical significance.

The present inventors recognize from experience that when mixing nematic liquid crystalline compounds having a small dielectric anisotropy and relatively small absolute values of the positive and negative components ($\epsilon_{\|}$, $\epsilon_{\perp}$) of their dielectric constants (to be referred to as $N_s$-type liquid crystals) with nematic liquid crystalline compounds having a large dielectric anisotropy and relatively large absolute values of the positive and negative components of their dielectric constants and/or their non-liquid crystalline compounds (to be referred to as $N_L$-type liquid crystals and/or homologs thereof), their mutual solubility poses problems. Specifically, these problems are summarized in (1) and (2) below.

(1) When the ratio of the $N_L$-type liquid crystals and/or homologs thereof to the $N_s$-type liquid crystals is increased, crystals appear in the resulting mixture.

(2) The mesomorphic range of the mixture becomes narrow, and the C→N transition temperature shifts to a high temperature side.

Since the above undesirable phenomena generally occur when known nematic liquid crystalline compounds are used, special combinations of the $N_s$-type liquid crystals and the $N_L$-type liquid crystals and/or homologs thereof must be chosen by considering their mutual solubility. Since the compounds of formula (I) in accordance with this invention have very good solubility in the additional components, the present invention is free from the defects associated with the known nematic liquid crystalline compositions.

The following Material Production Examples, Examples, and Comparative Example illustrate the present invention specifically.

Figure 2:
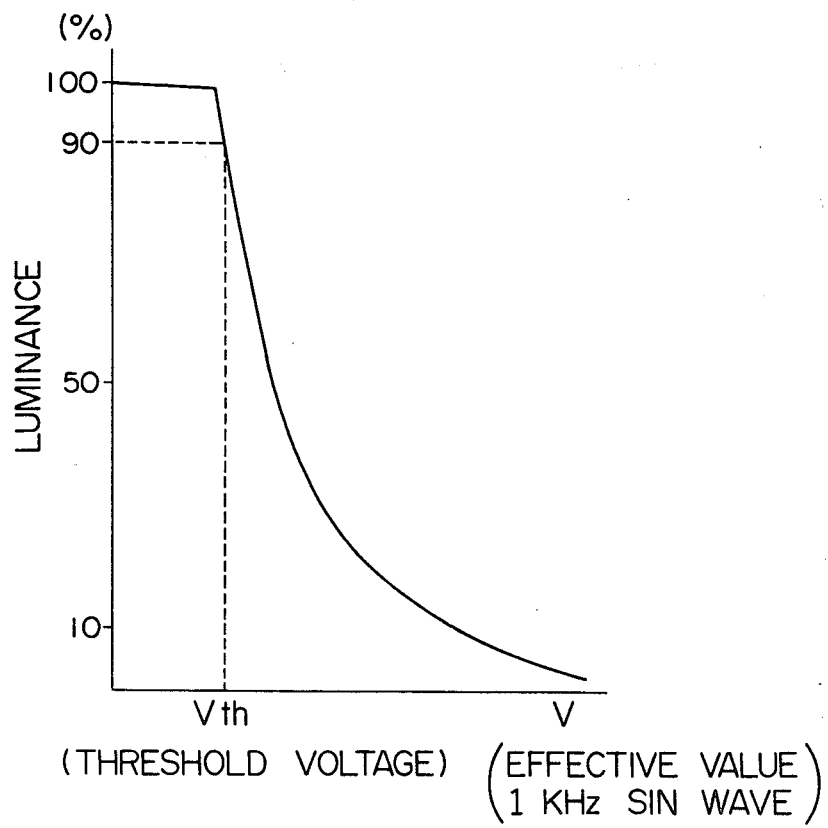
Figure 3:
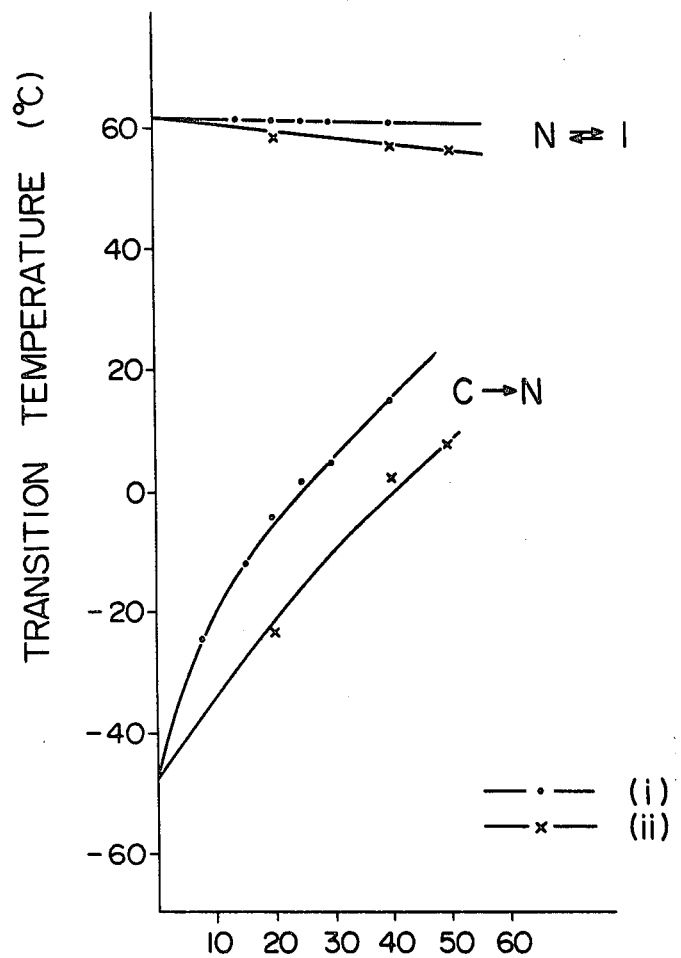
Figure 4:
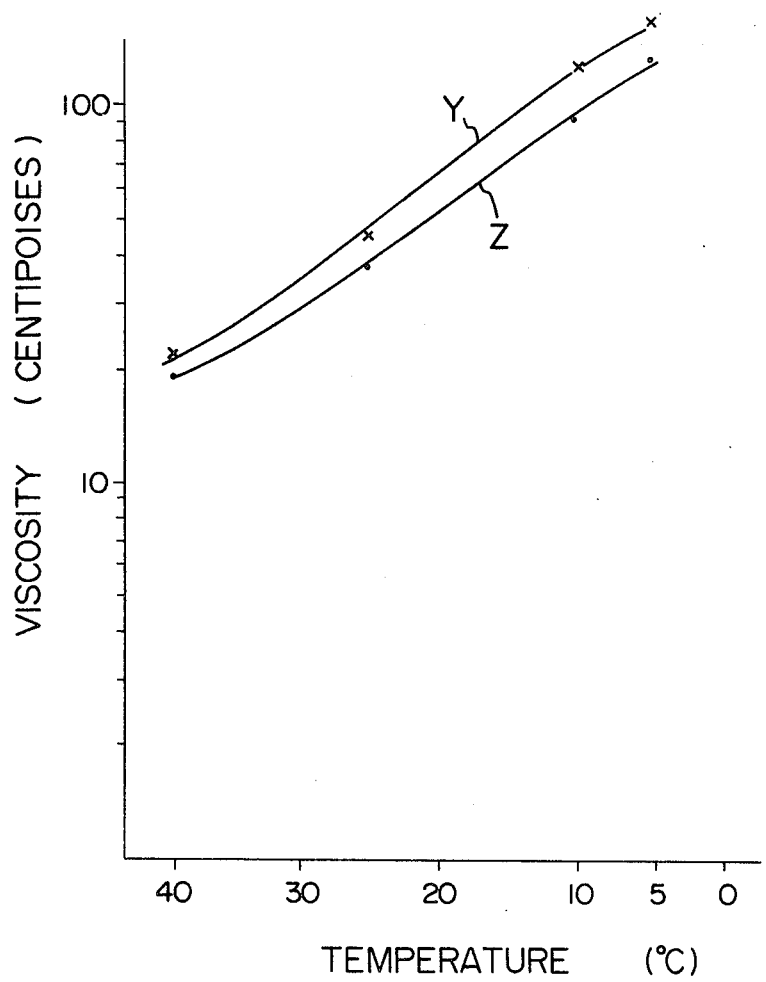

In the accompanying drawings, FIG. 1 is a cross-sectional view of a cell used in measuring threshold voltages in Examples; FIG. 2 is a graph showing the definition of a threshold voltage; FIG. 3 is a graph showing the properties of known mixed liquid crystalline compositions; and FIG. 4 is a graph showing the relation between the temperature and the viscosity of a mixed liquid crystalline composition of this invention.

MATERIAL PRODUCTION EXAMPLE 1

The compound of the formula

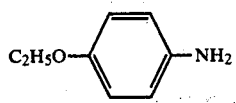

(137 g; 1 mole) was mixed with 200 cc of water, and 215 cc (2.5 moles) of conc. hydrochloric acid was gradually added dropwise to the resulting mixture. After the addition, the mixture was reacted at 50° to 60° C. for 30 minutes. A solution of 71.1 g (1 mole) of 97% sodium nitrite in 200 cc of water was added dropwise to the reaction mixture. After the addition, the mixture was reacted for 1 hour. At this time, the reaction temperature was maintained at less than 5° C. Potassium xanthogenate (321 g; 2 moles) was dissolved in 400 cc of water, and while maintaining the solution at 45° to 50° C., the reaction product was added dropwise over the course of 3 hours. After the addition, the mixture was reacted at the above temperature for 1 hour. The reaction product was extracted with diethyl ether. The extract was washed with a 3% aqueous solution of sodium hydroxide, dried over anhydrous sodium sulfate, and distilled to remove the ether. The reaction product was then dissolved in 1,000 ml of ethanol, and while refluxing the solution, 224.4 g (4 moles) of sodium hydroxide was gradually added. After the addition, the mixture was reacted for 3.5 hours.

Ethanol was distilled off from the reaction mixture, and water was added to the residue. The mixture was acidified with 6 N sulfuric acid, and then the reaction product was extracted with diethyl ether. The extract was washed with water, dried over anhydrous sodium sulfate, and distilled to afford 86.2 g (0.56 mole) of the following compound in a yield of 56.0%.

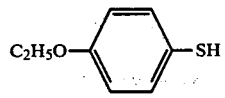

b.p. 90°–91° C./1.5 mmHg

MATERIAL PRODUCTION EXAMPLES 2 to 4

The procedure of Material Production Example 1 was repeated except that 1 mole of each of the following compounds,

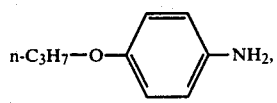

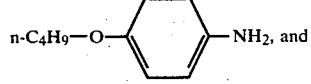

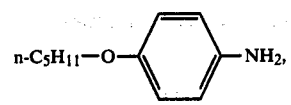

was used instead of the compound

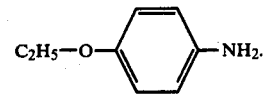

Thus, the compounds shown in Table 2 were obtained.

Table 2

| Production Example No. | Yield (%) | Compound |
|---|---|---|
| 2 | 52.8 | n-C$_3$H$_7$—O—⟨⟩—SH<br>b.p. 99° C./3 mmHg |
| 3 | 54.1 | n-C$_4$H$_9$—O—⟨⟩—SH<br>b.p. 104°–105° C./3 mmHg |
| 4 | 50.7 | n-C$_5$H$_{11}$—O—⟨⟩—SH<br>b.p. 126°–128° C./2 mmHg |

MATERIAL PRODUCTION EXAMPLE 5

The procedure of Material Production Example 1 was repeated except that 1 mole of the compound of the formula

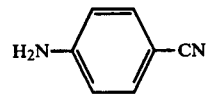

was used instead of 1 mole of the compound of the formula

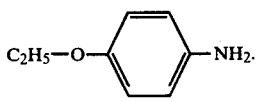

Thus, 62.1 g (0.46 mole) of the following compound was obtained in a yield of 46%.

b.p. 118°–119° C./3 mmHg

EXAMPLE 1

17.0 g (0.1 mole) of the compound

was dissolved in 50 g of thionyl chloride, and the mixture was reacted under reflux for 1 hour. The excess of the thionyl chloride was distilled off. Then, the reaction product was dissolved in 50 ml of diethyl ether, and to this solution was added at 0° C., 15.4 g (0.1 mole) of the compound

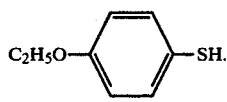

Subsequently, at −10° C., 20 g of pyridine was added dropwise. After the addition, this mixture was reacted for 1 hour under reflux. The reaction mixture was washed with dilute hydrochloric acid and water and dried over anhydrous sodium sulfate. Then, the ether was distilled off from this reaction mixture. The resulting product was recrystallized from methanol to afford 19.8 g (0.065 mole) of the following compound in a yield of 65%.

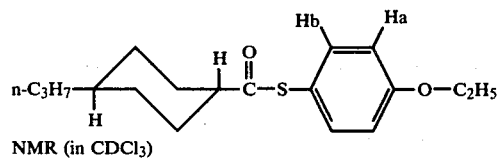

NMR (in CDCl$_3$)
δ (PPM):

0.96 (t, 3H, CH$_3$—C—C—)

1.18 (m, 4H, —(CH$_2$)$_2$—)

1.36 (t, 3H, CH$_3$—C—O—)

− 2.2 (m, 9H, H of the cyclohexane ring)
2.47 (t, t, 1H, Cyclohexane ring C=O gem. axi. proton)

3.97 (q, 2H, —CH$_2$—O—)
6.84 (d, 2H, Ha)
7.23 (d, 2H, Hb)

EXAMPLES 2 to 5

The procedure of Example 1 was repeated except that 0.1 mole of each of the following compounds was used instead of the compound

used in Example 1.

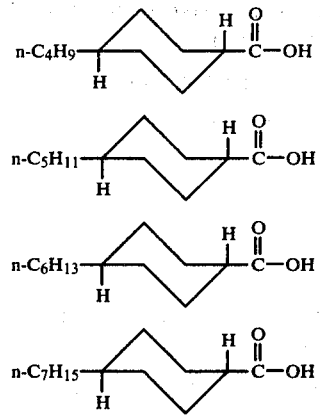

Thus, the compounds shown in Table 3 were obtained.

Table 3

R—⌬—C(=O)—S—⌬—O—C$_2$H$_5$ (Hb, Ha)

| Ex. No. | R | Yield (%) | NMR (in CDCl$_3$) |
|---|---|---|---|
| 2 | n-C$_4$H$_5$— | 61.2 | δ(PPM): 0.95 (t, 3H, CH$_3$—C—C—) 1.20 (s, 6H, —(CH$_2$)$_3$—) 1.35 (t, 3H, CH$_3$—C—O—) −2.2 (m, 9H, H of the cyclohexane ring proton) 2.47 (t, t, 1H, cyclohexane ring C=O gem.axi. proton) 3.97 (q, 2H, —CH$_2$—O—) 6.84 (d, 2H, Ha) 7.23 (d, 2H, Hb) |
| 3 | n-C$_5$H$_{11}$— | 62.3 | δ(PPM): 0.96 (t, 3H, CH$_3$—C—C—) 1.22 (s, 8H, —(CH$_2$)$_4$—) 1.36 (t, 3H, CH$_3$—C—O—) −2.2 (m, 9H, H of the cyclohexane ring) 2.47 (t, t, 1H, cyclohexane ring C=O gem.axi. proton) 3.97 (q, 2H, —CH$_2$—O—) 6.84 (d, 2H, Ha) 7.23 (d, 2H, Hb) |
| 4 | n-C$_6$H$_{13}$— | 65.9 | δ(PPM): |

Table 3-continued

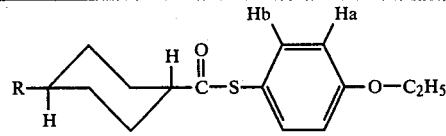

| Ex. No. | R | Yield (%) | NMR (in CDCl₃) |
|---|---|---|---|
| 5 | n-C₇H₁₅— | 63.5 | 0.96 (t, 3H, CH₃—C—C—)<br>1.22 (s, 10H, —(CH₂)₅—)<br>1.36 (t, 3H, CH₃—C—O—)<br>—2.2 (m, 9H, H of the cyclohexane ring)<br>2.47 (t, t, 1H, cyclohexane ring <br>\\C=O gem.axi. proton)<br>3.97 (q, 2H, —CH₂—O—)<br>6.84 (d, 2H, Ha)<br>7.23 (d, 2H, Hb)<br>δ(PPM):<br>0.96 (t, 3H, CH₃—C—C—)<br>1.22 (s, 12H, —(CH₂)₆—)<br>1.36 (t, 3H, CH₃—C—O—)<br>—2.2 (m, 9H, H of the cyclohexane ring)<br>2.47 (t, t, 1H, cyclohexane ring <br>\\C=O gem.axi. proton)<br>3.97 (q, 2H, —CH₂—O—)<br>6.87 (d, 2H, Ha)<br>7.23 (d, 2H, Hb) |

EXAMPLE 6

17.0 g (0.1 mole) of the compound

was dissolved in 50 g of thionyl chloride. The mixture was reacted under reflux for 1 hour, and the excess of thionyl chloride was distilled off. The resulting product was dissolved in 50 ml of diethyl ether, and to this solution was added 16.8 g (0.1 mole) of the compound

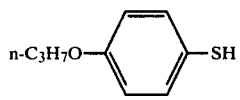

and subsequently, 20 g of pyridine was added dropwise at −10° C. After the addition, the mixture was reacted under reflux for 1 hour. Then, the reaction mixture was washed with dilute hydrochloric acid and water, and dried over anhydrous sodium sulfate. Then, the diethyl ether was distilled off from the reaction mixture. Recrystallization of the reaction product from methanol afforded 20.3 g (0.0634 mole) of the following compound in a yield of 63.4%.

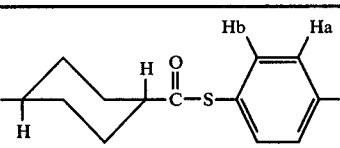

NMR (in CDCl₃)
δ(PPM):

| | |
|---|---|
| 0.90 | (t, 3H, CH₃—C—C—cyclohexyl) |
| 1.01 | (t, 3H, CH₃—C—C—O—) |
| 1.1–1.5 | (m, 6H, —CH₂—) |
| —2.2 | (m, 9H, H of the cyclohexane ring) |
| 2.50 | (t, t, 1H, cyclohexane ring \\C=O gem.axi. proton) |
| 3.95 | (t, 2H, —CH₂—O—) |
| 6.90 | (d, 2H, Ha) |
| 7.32 | (d, 2H, Hb) |

EXAMPLES 7 to 10

The procedure of Example 6 was repeated except that 0.1 mole of each of the following compounds was used instead of the compound

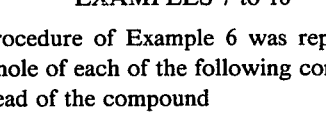

used in Example 6.

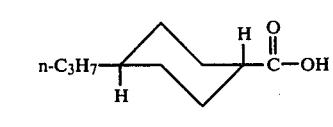

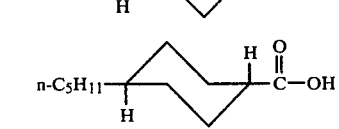

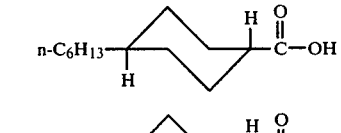

The compounds shown in Table 4 were obtained.

Table 4

| Ex. No. | R | Yield (%) | NMR (in CDCl₃) |
|---|---|---|---|
| 7 | n-C$_4$H$_9$— | 59.4 | δ(PPM): 0.90 (t, 3H, CH$_3$—C—C—C—) <br> 1.01 (t, 3H, CH$_3$—C—C—O—) <br> 1.1–1.5 (m, 8H, —CH$_2$—) <br> –2.2 (m, 9H, H of the cyclohexane ring) <br> 2.52 (t, t, 1H, cyclohexane ring \C=O gem.axi. proton) <br> 3.94 (t, 2H, —CH$_2$—O—) <br> 6.91 (d, 2H, Ha) <br> 7.31 (d, 2H, Hb) |
| 8 | n-C$_5$H$_{11}$— | 61.7 | δ(PPM): 0.91 (t, 3H, CH$_3$—C—C—C—) <br> 1.01 (t, 3H, CH$_3$—C—C—O—) <br> 1.1–1.5 (m, 10H, —CH$_2$—) <br> –2.2 (m, 9H, H of the cyclohexane ring) <br> 2.52 (t, t, 1H, cyclohexane ring \C=O gem.axi. proton) <br> 3.94 (t, 2H, —CH$_2$—O—) <br> 6.91 (d, 2H, Ha) <br> 7.32 (d, 2H, Hb) |
| 9 | n-C$_6$H$_{13}$— | 65.0 | δ(PPM): 0.91 (t, 3H, CH$_3$—C—C—C—) <br> 1.01 (t, 3H, CH$_3$—C—C—O—) <br> 1.1–1.5 (m, 12H, —CH$_2$—) <br> –2.2 (m, 9H, H of the cyclohexane ring) <br> 2.52 (t, t, 1H, cyclohexane ring \C=O gem.axi. proton) <br> 3.94 (t, 2H, —CH$_2$—O—) <br> 6.91 (d, 2H, Ha) <br> 7.32 (d, 2H, Hb) |
| 10 | n-C$_7$H$_{13}$— | 63.3 | δ(PPM): 0.91 (t, 3H, CH$_3$—C—C—C—) <br> 1.01 (t, 3H, CH$_3$—C—C—O—) <br> 1.1–1.5 (m, 14H, —CH$_2$—) <br> –2.2 (m, 9H, H of the cyclohexane ring) <br> 2.52 (t, t, 1H, cyclohexane ring \C=O gem.axi. proton) <br> 3.94 (t, 2H, —CH$_2$—O—) <br> 6.91 (d, 2H, Ha) <br> 7.32 (d, 2H, Hb) |

EXAMPLE 11

17.0 g (0.1 mole) of the compound

was dissolved in 50 g of thionyl chloride, and the mixture was reacted under reflux for 1 hour. The excess of thionyl chloride was distilled off. Then, the resulting reaction product was dissolved in 50 ml of diethyl ether, and to the solution was added 18.2 g (0.1 mole) of the compound

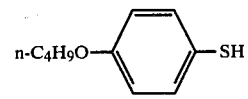

at 0° C. Then, 20 g of pyridine was added dropwise at −10° C. After the addition, the mixture was reacted under reflux for 1 hour. The reaction mixture was washed with dilute hydrochloric acid and water, and dried. The diethyl ether was then distilled off from the reaction mixture. Recrystallization of the reaction product from methanol afforded 21.6 g (0.0647 mole) of the following compound in a yield of 64.7%.

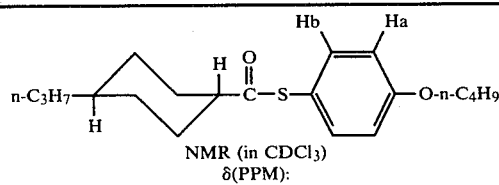

NMR (in CDCl₃) δ(PPM):

0.90 (t, 3H, CH$_3$—C—C—⟨cyclohexyl⟩—)

0.98 (t, 3H, CH$_3$—C—C—C—O—)

1.1–1.5 (m, 8H, —CH$_2$—)

–2.2 (m, 9H, H of the cyclohexane ring)

2.52 (t, t, 1H, cyclohexane ring

-continued

[Structure: cyclohexane ring with n-C3H7 and H substituents, connected via CH with H to C(=O)-S-phenyl with Hb, Ha positions and O-n-C4H9]

NMR (in CDCl3)
δ(PPM):

\C=O gem.axi. proton)
/

3.97 (t, 2H, —CH2—O—)
6.90 (d, 2H, Ha)
7.32 (d, 2H, Hb)

EXAMPLES 12 to 15

The procedure of Example 11 was repeated except that 0.1 mole of each of the following compounds was used instead of the compound

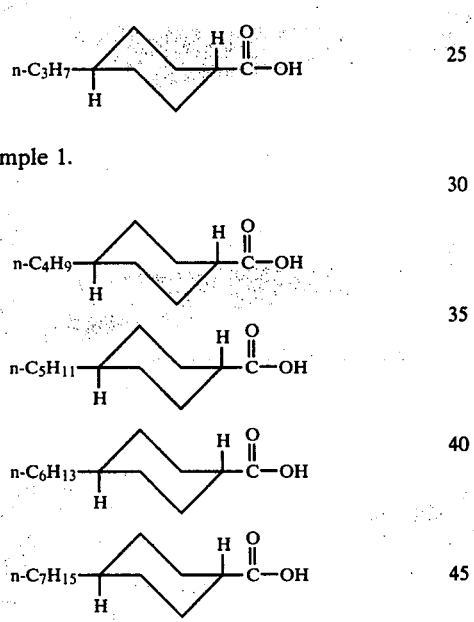

used in Example 1.

Thus, the compounds shown in Table 5 were obtained.

Table 5

[Structure: R-cyclohexane-H, CH with H, C(=O)-S-phenyl (Hb, Ha)-O-n-C4H9]

| Example No. | R | Yeild (%) | NMR (in CDCl3) |
|---|---|---|---|
| 12 | n-C4H9— | 64.1 | δ(PPM): |

0.90 (t, 3H, CH3—C—C—C—⟨cyclohexyl⟩—)

0.98 (t, 3H, CH3—C—C—C—O—)

Table 5-continued

[Structure: R-cyclohexane-H, CH with H, C(=O)-S-phenyl (Hb, Ha)-O-n-C4H9]

| Example No. | R | Yeild (%) | NMR (in CDCl3) |
|---|---|---|---|
| | | | 1.1–1.5 (m, 10H, —CH2—) |
| | | | –2.2 (m, 9H, H of the cyclohexane ring) |
| | | | 2.52 (t, t, 1H, cylohexane ring |

\C=O gem.axi. proton)
/

3.97 (t, 2H, —CH2—O—)
6.89 (d, 2H, Ha)
7.31 (d, 2H, Hb)

| 13 | n-C5H11— | 62.8 | δ(PPM): |

0.91 (t, 3H, CH3—C—C—C—C—)

0.99 (t, 3H, CH3—C—C—C—O—)

1.1–1.5 (m, 12H, —CH2—)
–2.2 (m, 9H, H of the cyclohexane ring)
2.50 (t, t, 1H, cylohexane ring \C=O gem.axi. proton)
/

3.97 (t, 2H, —CH2—O—)
6.90 (d, 2H, Ha)
7.32 (d, 2H, Hb)

| 14 | n-C6H13— | 63.7 | δ(PPM): |

0.91 (t, 3H, CH3—C—C—C—C—)

0.99 (t, 3H, CH3—C—C—C—O—)

1.1–1.5 (m, 14H, —CH2—)
–2.2 (m, 9H, H of the cyclohexane ring)
2.50 (t, t, 1H, cylohexane ring \C=O gem.axi. proton)
/

3.97 (t, 2H, —CH2—O—)
6.90 (d, 2H, Ha)
7.32 (d, 2H, Hb)

| 15 | n-C7H15— | 63.2 | δ(PPM): |

0.91 (t, 3H,CH3—C—C—C—C—)

0.99 (t, 3H, CH3—C—C—C—O—)

1.1–1.5 (m, 16H, —CH2—)
–2.2 (m, 9H, H of the cyclohexane ring)
2.50 (t, t, 1H, cylohexane ring Table 5-continued

| | Hb | Ha | | |
|---|---|---|---|---|
| R─⟨cyclohexane⟩─C(=O)─S─⟨phenyl⟩─O-n-C₄H₉ | | | | |

| Example No. | R | Yield (%) | NMR (in CDCl₃) |
|---|---|---|---|

>C=O gem.axi. proton)

3.97 (t, 2H, —CH₂—O—)
6.90 (d, 2H, Ha)
7.32 (d, 2H, Hb)

EXAMPLE 16

17.0 g (0.1 mole) of the compound of formula

was dissolved in 50 g of thionyl chloride, and the mixture was reacted under reflux for 1 hour. The excess of thionyl chloride was distilled off, and the resulting product was dissolved in 50 ml of diethyl ether. To this solution was added 19.6 g (0.1 mole) of the compound

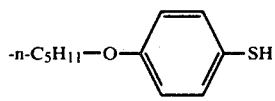

at 0° C., and subsequently, 20 g of pyridine was added at −10° C. After the addition, the mixture was reacted under reflux for 1 hour. The reaction mixture was washed with dilute hydrochloric acid and water, and anhydrous sodium sulfate. Then, the diethyl ether was distilled off from the reaction mixture. Recrystallization of the reaction product from methanol afforded 21.5 g (0.0618 mole) of the following compound in a yield of 61.8%.

n-C₃H₇─⟨cyclohexane⟩─C(=O)─S─⟨phenyl⟩─O—n-C₅H₁₁

NMR (in CDCl₃)
δ(PPM):

| 0.90 | (t, 3H, CH₃—C—C—⟨cyclohexane⟩—) |
| 0.95 | (t, 3H, CH₃—C—C—C—C—O—) |
| 1.1–1.5 | (m, 10H, —CH₂—) |
| −2.2 | (m, 9H, H of the cyclohexane ring) |
| 2.52 | (t, t, 1H cyclohexane ring >C=O gem.axi. proton) |
| 3.98 | (t, 2H, —CH₂—O—) |
| 6.91 | (d, 2H, Ha) |
| 7.32 | (d, 2H, Hb) |

EXAMPLES 17 to 20

The procedure of Example 16 was repeated except that 0.1 mole of each of the following compounds was used instead of the compound

used in Example 16.

Thus, the compounds shown in Table 6 were obtained.

Table 6

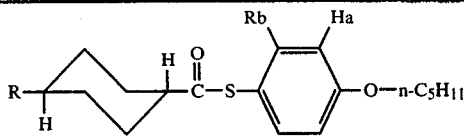

| Example No. | R | Yield (%) | NMR (in CDCl₃) |
|---|---|---|---|
| 17 | n-C₄H₉— | 63.5 | δ (PPM): 0.90 (t, 3H, CH₃—C—C—C—cyclohexyl) 0.95 (t, 3H, CH₃—C—C—C—C—O—) 1.1–1.5 (m, 12H, —CH₂—) –2.2 (m, 9H, H of the cyclohexane ring) 2.52 (t,t, 1H, cyclohexane ring \C=O gem.axi. proton) 3.98 (t, 2H, —CH₂—O—) 6.91 (d, 2H, Ha) 7.32 (d, 2H, Hb) |
| 18 | n-C₅H₁₁— | 64.9 | δ (PPM): 0.91 (t, 3H, CH₃—C—C—C—C—cyclohexyl) 0.96 (t, 3H, CH₃—C—C—C—C—O—) 1.1–1.5 (m, 14H, —CH₂—) –2.2 (m, 9H, H of the cyclohexane ring) 2.50 (t,t, 1H, cyclohexane ring \C=O gem.axi. proton) 3.98 (t, 2H, —CH₂—O—) 6.91 (d, 2H, Ha) 7.32 (d, 2H, Hb) |
| 19 | n-C₆H₁₃— | 63.0 | δ (PPM): 0.90 (t, 3H, CH₃—C—C—C—C—cyclohexyl) 0.95 (t, 3H, CH₃—C—C—C—C—O—) 1.1–1.5 (m, 16H, —CH₂—) –2.2 (m, 9H, H of the cyclohexane ring) 2.50 (t,t, 1H, cyclohexane ring \C=O gem.axi. proton) 3.98 (t, 2H, CH₂—O—) 6.91 (d, 2H, Ha) 7.32 (d, 2H, Hb) |
| 20 | n-C₇H₁₅- | 65.2 | δ(PPM): 0.90 (t, 3H, CH₃—C—C—C—C—cyclohexyl) |

Table 6-continued

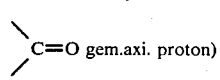

| Example No. | R | Yield (%) | NMR (in CDCl₃) |
|---|---|---|---|

0.95 (t, 3H, CH₃—C—C—C—C—O—)

1.1–1.5 (m, 18H, —CH₂—)
–2.2 (m, 9H, H of the cyclohexane ring)
2.50 (t,t, 1H, cyclohexane ring \>C=O gem.axi. proton)

3.98 (t, 2H, —CH₂—O—)
6.91 (d, 2H, Ha)
7.32 (d, 2H, Hb)

EXAMPLE 21

17.0 g (0.1 mole) of the compound

was dissolved in 50 g of thionyl chloride, and the mixture was reacted under reflux for 1 hour. The excess of thionyl chloride was distilled off. The resulting reaction product was dissolved in 50 ml of diethyl ether, and to this solution was added 13.5 g (0.1 mole) of the compound

Subsequently, 20 g of pyridine was added drop-wise at −10° C. After the addition, the mixture was reacted under reflux for 1 hour. Then, the reaction mixture was washed with dilute hydrochloric acid and water, and dried over anhydrous sodium sulfate. Then, the diethyl ether was distilled off from the reaction mixture. Recrystallization of the reaction product from methanol afforded 17.5 g (0.0610 mole) of the following compound in a yield of 61.0%.

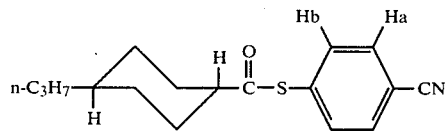

NMR (in CDCl₃)
δ (PPM):

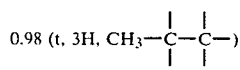

-continued
1.23 (m, 4H, —(CH₂)₂—)
–2.2 (m, 9H, H of the cyclohexane ring)
2.53 (t,t, 1H, cyclohexane ring \>C=O gem.axi. proton)

7.62 (d, 2H, Ha)
7.47 (d, 2H, Hb)

The procedure of Example 21 was repeated except that 0.1 mole of each of the following compounds was used instead of the compound

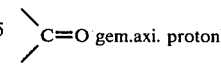

used in Example 21.

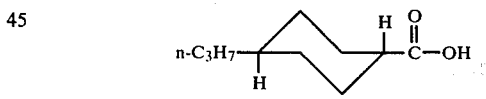

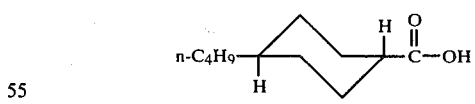

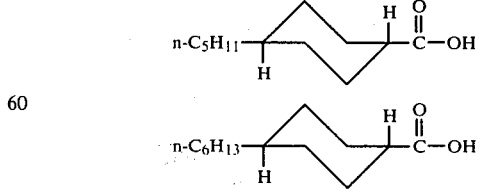

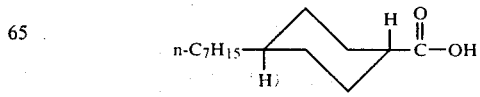

Table 7

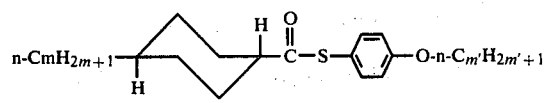

| Example No. | R | Yield (%) | NMR (in CDCl₃) |
|---|---|---|---|
| 22 | n-C₄H₉— | 60.4 | δ(PPM): 0.98 (t, 3H, CH₃—C—C—) 1.23 (s, 6H, —(CH₂)₃—) −2.2 (m, 9H, H of the cyclohexane ring) 2.53 (t,t, 1H, cyclohexane ring \C=O gem.axi. proton) 7.62 (2H, Ha) 7.47 (d, 2H, Hb) |
| 23 | n-C₅H₁₁— | 62.3 | δ (PPM): 0.98 (t, 3H, CH₃—C—C—) 1.23 (s, 8H, —(CH₂)₄—) −2.2 (m, 9H, H of the cyclohexane ring) 2.53 (t,t, 1H, cyclohexane ring \C=O gem.axi. proton) 7.62 (d, 2H, Ha) 7.47 (d, 2H, Hb) |
| 24 | n-C₆H₁₃— | 63.1 | δ (PPM): 0.98 (t, —3H, CH₃—C—C—) 1.23 (s, 10H, —(CH₂)₃—) −2.2 (m, 9H, H of the cyclohexane ring) 2.53 (t,t, 1H, cyclohexane ring \C=O gem.axi. proton) 7.62 (d, 2H, Ha) 7.47 (d, 2H, Hb) |
| 25 | n-C₇H₁₅— | 61.8 | δ (PPM): 0.98 (t, 3H, CH₃—C—C—) 1.23 (s, 12H, —(CH₂)₆—) −2.2 (m, 9H, H of the cyclohexane ring) 2.53 (t,t, 1H, cyclohexane ring \C=O gem.axi. proton) 7.62 (d, 2H, Ha) 7.47 (d, 2H, Hb) |

EXAMPLES 26 to 64

Nematic liquid crystalline compositions in accordance with this invention were prepared by mixing two or three compounds of formula (I), and their physical properties were measured. The results are shown in Table 8. In the table, m-m′ is an abbreviation for a compound of the formula $$\text{n-C}_m\text{H}_{2m+1}-\text{[cyclohexane]}-\overset{\text{O}}{\underset{}{\text{C}}}-\text{S}-\text{[phenyl]}-\text{O-n-C}_{m'}\text{H}_{2m'+1}$$

For example, 3–5 means a compound of the above formula in which m is 3 and m′ is 5.

Table 8

| Example No. | Abbreviation | Mixed liquid crystal composition (mole %) m-m′ | m-m′ | m-m′ | Transition temperature (°C.) C→N | N⇌I |
|---|---|---|---|---|---|---|
| 26 | — | 3-5 (35) | 5-2 (65) | — | 35 | 60 |
| 27 | A | 3-5 (50) | 5-2 (50) | — | 26 | 59 |
| 28 | — | 3-5 (65) | 5-2 (35) | — | 35 | 57 |
| 29 | — | 3-5 (50) | 5-5 (50) | — | 51 | 53 |
| 30 | — | 5-2 (65) | 7-2 (35) | — | 39 | 69 |
| 31 | — | 5-2 (50) | 7-2 (50) | — | 42 | 69 |
| 32 | — | 3-2 (33.3) | 3-3 (33.3) | 4-2 (33.3) | 38 | 57 |
| 33 | — | 3-2 (33.3) | 3-3 (33.3) | 5-2 (33.3) | 24 | 56.5 |
| 34 | — | 3-2 (33.3) | 5-2 (33.3) | 4-3 (33.3) | 24 | 54.5 |
| 35 | B | 3-2 (33.3) | 5-2 (33.3) | 4-5 (33.3) | 9 | 54.5 |
| 36 | — | 3-2 (40) | 5-2 (40) | 4-5 (20) | 21 | 61 |
| 37 | — | 3-2 (40) | 5-2 (20) | 4-5 (40) | 25 | 53.5 |
| 38 | — | 3-2 (20) | 5-2 (40) | 4-5 (40) | 26 | 55.5 |
| 39 | C | 3-2 (33.3) | 5-2 (33.3) | 3-5 (33.3) | 18 | 59.5 |
| 40 | — | 3-2 (33.3) | 5-2 (33.3) | 7-2 (33.3) | 21 | 56 |
| 41 | — | 3-2 (33.3) | 4-2 (33.3) | 5-2 (33.3) | 29 | 60.5 |
| 42 | — | 3-2 (33.3) | 4-2 (33.3) | 7-2 (33.3) | 27 | 60.5 |
| 43 | — | 3-2 (33.3) | 4-2 (33.3) | 6-2 (33.3) | 29 | 57 |
| 44 | — | 3-2 (33.3) | 5-2 (33.3) | 3-4 (33.3) | 16 | 59.5 |
| 45 | — | 3-2 (33.3) | 5-2 (33.3) | 4-4 (33.3) | 22 | 56.5 |
| 46 | — | 3-2 (33.3) | 5-2 (33.3) | 5-4 (33.3) | 28 | 61.5 |
| 47 | — | 3-2 (33.3) | 5-2 (33.3) | 6-3 (33.3) | 23 | 56 |
| 48 | — | 3-2 (33.3) | 4-2 (33.3) | 3-4 (33.3) | 21 | 53 |
| 49 | — | 3-2 (33.3) | 4-2 (33.3) | 3-5 (33.5) | 26 | 52 |
| 50 | — | 3-2 (33.3) | 4-2 (33.3) | 4-5 (33.3) | 13 | 42 |
| 51 | — | 3-2 (33.3) | 4-2 (33.3) | 5-4 (33.3) | 25 | 56 |
| 52 | — | 4-2 (33.3) | 5-2 (33.3) | 7-2 (33.3) | 32 | 65 |
| 53 | — | 4-2 (33.3) | 5-2 (33.3) | 3-3 (33.3) | 25 | 54.5 |
| 54 | — | 4-2 (33.3) | 5-2 (33.3) | 3-4 (33.3) | 18 | 49 |
| 55 | — | 4-2 (33.3) | 5-2 (33.3) | 3-5 (33.3) | 18 | 57 |
| 56 | — | 4-2 (33.3) | 5-2 (33.3) | 4-3 (33.3) | 31 | 52.5 |
| 57 | — | 4-2 (33.3) | 5-2 (33.3) | 4-4 (33.3) | 21 | 55.5 |
| 58 | — | 4-2 (33.3) | 5-2 (33.3) | 4-5 (33.3) | 17 | 52.5 |
| 59 | — | 5-2 (33.3) | 7-2 (33.3) | 4-3 (33.3) | 27 | 58.5 |
| 60 | — | 5-2 (33.3) | 7-2 (33.3) | 4-5 (33.3) | 24.5 | 59 |
| 61 | — | 5-2 (33.3) | 5-3 (33.3) | 5-5 (33.3) | 34 | 57.5 |
| 62 | — | 5-2 (33.3) | 7-2 (33.3) | 3-5 (33.3) | 28 | 63 |
| 63 | — | 5-2 (33.3) | 4-3 (33.3) | 4-5 (33.3) | 25 | 51.5 |
| 64 | — | 7-5 (33.3) | 4-5 (33.3) | 3-2 (33.3) | 28 | 49.5 |

As is clear from a comparison of Table 1 with Table 8, each of the mixed crystals in Table 8 has a broadened mesomorphic range near room temperature over the individual liquid crystals which constitute the mixture.

These mixed liquid crystals are chemically stable, do not decompose by moisture, light, etc., are colorless, can perform a clear display, and have a viscosity of as low as 30 centipoises (25° C.). Hence, these mixed liquid crystals are very advantageous in high-speed response. In addition, they have superior solubility in other nematic liquid crystalline compounds and/or homologous non-liquid crystalline compounds. Accordingly, the mixed liquid crystals shown in Table 8 are very effective as matrix liquid crystals. For example, as shown in the following Example, practical liquid crystals of higher performance can be produced by mixing these mixed liquid crystals with other nematic liquid crystalline compounds and/or homologous non-liquid crystalline compounds.

EXAMPLES 65 to 76

Nematic liquid crystalline compositions of this invention usable in FEM cells were prepared by mixing the mixed liquid crystal B shown in Table 8 as a matrix with $N_p$-type liquid crystals and/or $N_p$-type liquid crystal homologs, and their physical properties were measured. The results are shown in Table 9.

The threshold voltages $V_{th}$ in the table were measured by the following method.

A cell including an obliquely vacuum-deposited film of SiO as an alignment control film and having a cell clearance of 10 microns was used. The applied voltage was 1 KHz (sin waves), and the observing light was a prependicularly transmitted glow light, and the measuring temperature was 25° C. The cross-sectional view of the cell is shown in FIG. 1 in which the reference numerals 1 and 1' represents polarizing plates; 2 and 2', glass plates; 3 and 3', alignment control films; 4 and 4', transparent electrodes; 5 and 5', spacers; and 6, a nematic liquid crystalline composition.

The definition of the threshold voltage $V_{th}$ is shown in FIG. 2.

In the column of "Transition temperature" in Table 9, −25* shows that the mixed liquid crystal did not crystallize when it was allowed to stand for a day and a night at −60° C. and then allowed to stand in a refrigerating chamber at −25° C. for 10 days, but remained nematic liquid crystalline. This is the same in the subsequent Tables.

Table 9

| Example No. | Matrix liquid crystal | $N_p$-type liquid crystal and/or homolog of $N_p$-type liquid crystal | Transition temperature (°C.) C→N | Transition temperature (°C.) N⇌I | Threshold voltage, $V_{th}$ (25° C.) (V) |
|---|---|---|---|---|---|
| 65 | B (60) | n-C₅H₇—⟨H⟩—⟨⟩—CN  (40) | −5 | 53 | 2.0 |
| 66 | B (60) | n-C₇H₁₅—⟨H⟩—⟨⟩—CN  (40) | 0 | 54 | 2.0 |
| 67 | B (90) | n-C₅H₁₁—⟨H⟩—⟨⟩—⟨⟩—CN  (10) | 2 | 67.5 | 3.8 |
| 68 | B (90) | n-C₃H₇—⟨H⟩—COO—⟨⟩—⟨⟩—CN  (10) | 1 | 70 | 3.7 |
| 69 | B (80) | n-C₄H₉—⟨⟩—COO—⟨⟩—CN  (10); n-C₃H₁₁—⟨⟩—COS—⟨⟩—CN  (10) | −6 | 58 | 1.6 |
| 70 | B (80) | n-C₅H₁₁—⟨⟩—⟨⟩—CN  (20) | −1 | 50 | 2.0 |
| 71 | B (80) | n-C₃H₇—⟨H⟩—COO—⟨⟩—CN  (20) | 0 | 55 | 2.5 |
| 72 | B (80) | n-C₄H₉—⟨⟩—COO—⟨⟩—CN  (20) | −5 | 49.5 | 1.6 |
| 73 | B (80) | n-C₅H₁₁—⟨⟩—COO—⟨⟩—CN  (20) | 0 | 51.5 | 2.1 |
| 74 | B (80) | n-C₅H₁₁—⟨⟩—COS—⟨⟩—CN  (20) | 2 | 58 | 2.1 |

Table 9-continued

| Example No. | Matrix liquid crystal | $N_p$-type liquid crystal and/or homolog of $N_p$-type liquid crystal | Transition temperature (°C.) C→N | N⇌I | Threshold voltage, $V_{th}$ (25° C.) (V) |
|---|---|---|---|---|---|
| 75 | B (20) | n-$C_6H_{13}$–[pyrimidine]–CH=N–[phenyl]–CN (20) | 9 | 47 | 1.7 |
| 76 | B (40) | n-$C_5H_{11}$–[H]–[phenyl]–CN (20) | −25* | 67.5 | 1.4 |
|  |  | n-$C_4H_9$–[phenyl]–COO–[phenyl]–CN (25) |  |  |  |
|  |  | n-$C_3H_7$–[phenyl]–COO–[phenyl(Cl)]–CN (5) |  |  |  |
|  |  | n-$C_3H_7$–[H]–COO–[phenyl]–[phenyl]–CN (10) |  |  |  |

The mixed liquid crystals shown in Table 9 have a broadened mesomorphic range than the matrix B, and it is especially noteworthy that the C→N transition temperatures of these mixed liquid crystals shift to a low temperature side. Similar results are obtained when the other mixed liquid crystals shown in Table 8 were used as a matrix liquid crystal. This demonstrates that the compounds of formula (I) forming the matrix and the $N_p$-type liquid crystals/and/or $N_p$-type liquid crystal homologs dissolve in each other very well.

The $N_p$-type liquid crystals and/or $N_p$-type liquid crystal homologs shown in Table 9 below to the $N_L$-type liquid crystals and/or $N_L$-type liquid crystal homologs defined hereinabove and the matrix liquid crystal B belongs to the $N_s$-type liquid crystal already defined hereinabove.

As stated hereinabove, when an $N_s$-type liquid crystal is mixed with an $N_L$-type liquid crystal and/or an $N_L$-type liquid crystal homolog, the mesomorphic range of the mixture is generally narrowed because of the insufficient mutual solubility of these, and the C→N transition temperature shifts to a high temperature side. Table 9 shows that the nematic liquid crystalline compositions exhibit a favorable phenomenon quite contrary to such a general tendency.

COMPARATIVE EXAMPLE

For comparison, a nematic liquid crystalline composition was prepared by mixing the following $N_s$-type matrix liquid crystal X with varying proportions of the liquid crystal (i) or (ii) which is of $N_L$-type and also $N_p$-type. The relation between the mixing proportions of the liquid crystal (i) or (ii) in these liquid crystalline compositions and their transition temperatures was measured. The results are shown in FIG. 3.

$CH_3$—O—[phenyl]—CH=N—[phenyl]—n-$C_4H_9$ (33.4 mole %)

$CH_3$—O—[phenyl]—CH=N—[phenyl]—n-$C_7H_{15}$ (33.4 mole %)

$C_2H_5$—O—[phenyl]—CH=N—[phenyl]—n-$C_4H_9$ (8.3 mole %)

$C_2H_5$—O—[phenyl]—CH=N—[phenyl]—n-$C_7H_{15}$ (8.3 mole %)

n-$C_4H_9$—O—[phenyl]—CH=N—[phenyl]—n-$C_4H_9$ (8.3 mole %)

n-$C_4H_9$—O—[phenyl]—CH=N—[phenyl]—n-$C_7H_{15}$ (8.3 mole %)

n-$C_3H_7$—[phenyl]—CH=N—[phenyl]—CN (i)

n-$C_7H_{15}$—[phenyl]—C(=O)—O—[phenyl]—CN (ii)

It is seen from FIG. 3 that as the mixing proportion of the $N_L$-type liquid crystal (i) or (ii) increases, the C-N transition temperature abruptly shifts to a high temperature side, and the mesomorphic range of the nematic liquid crystalline composition becomes abruptly narrow. This shows that the matrix liquid crystal X and the $N_L$-type liquid crystals (i) or (ii) have insufficient mutual solubility.

The liquid crystalline composition shown here as a comparison has average performances of known practical liquid crystals. The characteristics of the nematic liquid crystalline compositions of this invention will be more clearly understood in comparison with this Comparative Example.

EXAMPLES 77 to 90

Nematic liquid crystalline compositions of this invention were prepared by mixing the mixed liquid crystal A, B or C as a matrix with $N_n$-type liquid crystals and/or $N_n$-type liquid crystal homologs, and their physical properties were measured. The results are shown in Table 10.

Table 10

| Example No. | Abbreviation | Matrix liquid crystal | $N_n$-type liquid crystal and/or homolog of $N_n$-type liquid crystal | | Transition temperature (°C.) C→N | N⇌I |
|---|---|---|---|---|---|---|
| 77 | — | A (65) | 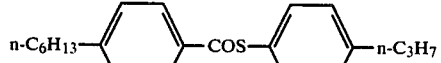 n-C$_6$H$_{13}$—⟨⟩—COS—⟨⟩—n-C$_3$H$_7$ | (35) | 12 | 46 |
| 78 | D | B (75) | 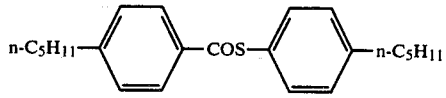 n-C$_5$H$_{11}$—⟨⟩—COS—⟨⟩—n-C$_5$H$_{11}$ | (25) | 1 | 50 |
| 79 | — | B (75) | 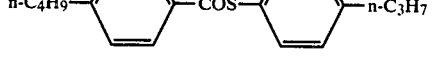 n-C$_4$H$_9$—⟨⟩—COS—⟨⟩—n-C$_3$H$_7$ | (25) | −2 | 43.5 |
| 80 | — | B (75) |  n-C$_5$H$_{11}$—⟨⟩—COS—⟨⟩—n-C$_4$H$_9$ | (25) | −1 | 45 |
| 81 | — | B (75) |  n-C$_7$H$_{15}$—⟨⟩—COS—⟨⟩—n-C$_5$H$_{11}$ | (25) | −3 | 41.5 |
| 82 | E | C (75) | 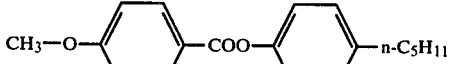 n-C$_5$H$_{11}$—⟨⟩—COS—⟨⟩—n-C$_5$H$_{11}$ | (25) | 6 | 53 |
| 83 | F | B (75) | 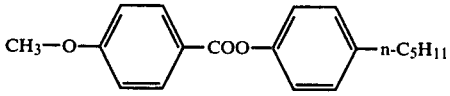 CH$_3$—O—⟨⟩—COO—⟨⟩—n-C$_5$H$_{11}$ | (25) | 10 | 52 |
| 84 | G | C (75) |  CH$_3$—O—⟨⟩—COO—⟨⟩—n-C$_5$H$_{11}$ | (25) | 13 | 56 |
| 85 | — | B (80) |  n-C$_6$H$_{13}$—⟨⟩—COO—⟨⟩—n-C$_4$H$_9$ | (20) | 5 | 43 |
| 86 | H | B (75) |  n-C$_5$H$_{11}$—⟨H⟩—COO-n-C$_5$H$_{11}$ | (25) | 11 | 50 |
| 87 | — | B (50) | 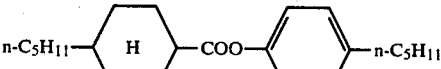 n-C$_5$H$_{11}$—⟨H⟩—COO—⟨⟩—n-C$_5$H$_{11}$ | (50) | 12 | 47 |
| 88 | I | B (50) | 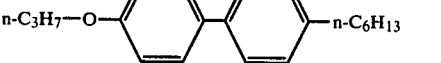 n-C$_4$H$_9$—⟨H⟩—COO—⟨⟩—O-n-C$_6$H$_{13}$  n-C$_5$H$_{11}$—⟨H⟩—COO—⟨⟩—n-C$_5$H$_{11}$ | (33) (17) | −4 | 57 |
| 89 | — | B (90) | 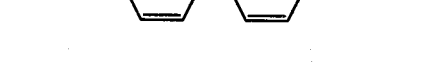 n-C$_3$H$_7$—O—⟨⟩—⟨⟩—n-C$_6$H$_{13}$ | (10) | 7 | 49.5 |

Table 10-continued

| | | Mixed liquid crystalline composition (mole %) | | Transition temperature (°C.) | |
|---|---|---|---|---|---|
| Example No. | Abbreviation | Matrix liquid crystal | $N_n$-type liquid crystal and/or homolog of $N_n$-type liquid crystal | C ⟶ N | N ⇌ I |
| 90 | — | B (75) | n-C₅H₁₁—⟨Ph⟩—COS—⟨Ph⟩—O-n-C₅H₁₁ (25) | −1 | 56 |

EXAMPLES 91 to 112

The mixed liquid crystals D, E, G, H and I shown in Table 10 and mixed liquid crystals J, K and L of the following compositions were used as matrices. These matrices were mixed with $N_p$-type liquid crystals and/or $N_p$-type liquid crystal homologs to form nematic liquid crystalline compositions of this invention. The physical properties of these compositions were measured, and the results are shown in Table 11.

The viscosities and temperatures of the mixed liquid crystal Y in Example 101 and the mixed liquid crystal Z of Example 105 were measured, and the results are shown in FIG. 4.

$$n\text{-}C_3H_7-\underset{H}{\bigcirc}-COS-\bigcirc-OC_2H_5 \quad (26.7 \text{ mole \%})$$

$$n\text{-}C_5H_{11}-\underset{H}{\bigcirc}-COS-\bigcirc-OC_2H_5 \quad (26.7 \text{ mole \%})$$

$$n\text{-}C_4H_9-\underset{H}{\bigcirc}-COS-\bigcirc-O-n\text{-}C_5H_{11} \quad (26.7 \text{ mole \%})$$

$$n\text{-}C_3H_7-\underset{H}{\bigcirc}-COO-\bigcirc-COO-\bigcirc-n\text{-}C_3H_7 \quad (20 \text{ mole \%})$$

⎫ J $$n\text{-}C_3H_7-\underset{H}{\bigcirc}-COS-\bigcirc-OC_2H_5 \quad (26.7 \text{ mole \%})$$

$$n\text{-}C_5H_{11}-\underset{H}{\bigcirc}-COS-\bigcirc-OC_2H_5 \quad (26.7 \text{ mole \%})$$

$$n\text{-}C_4H_9-\underset{H}{\bigcirc}-COS-\bigcirc-O-n\text{-}C_5H_{11} \quad (26.7 \text{ mole \%})$$

$$n\text{-}C_4H_9-\bigcirc-COO-\bigcirc-COO-\bigcirc-n\text{-}C_4H_9 \quad (20 \text{ mole \%})$$

⎫ K $$n\text{-}C_3H_7-\underset{H}{\bigcirc}-COS-\bigcirc-OC_2H_5 \quad (24 \text{ mole \%})$$

$$n\text{-}C_5H_{11}-\underset{H}{\bigcirc}-COS-\bigcirc-OC_2H_5 \quad (16 \text{ mole \%})$$

$$n\text{-}C_6H_9-\underset{H}{\bigcirc}-COS-\bigcirc-O-n\text{-}C_5H_{11} \quad (24 \text{ mole \%})$$

⎫ L

-continued

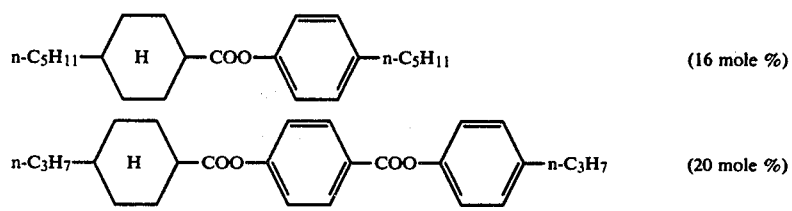

Table 11

| Example No. | Matrix liquid crystal | $N_p$-type liquid crystal and/or homolog of $N_p$-type liquid crystal | | Transition temperature (°C.) C→N | N⇌I | Threshold voltage, $V_{th}$ (25° C.) (V) |
|---|---|---|---|---|---|---|
| 91 | D (80) | n-C₃H₇—H—COO—⬡—⬡—CN | (10) | −7 | 69.5 | 2.3 |
|  |  | n-C₄H₉—⬡—COO—⬡—CN | (10) |  |  |  |
| 92 | E (80) | n-C₃H₇—H—COO—⬡—⬡—CN | (10) | −4 | 71.5 | 2.3 |
|  |  | n-C₄H₉—⬡—COO—⬡—CN | (10) |  |  |  |
| 93 | G (80) | n-C₃H₇—H—COO—⬡—⬡—CN | (10) | −5 | 73 | 2.3 |
|  |  | n-C₄H₉—⬡—COO—⬡—CN | (10) |  |  |  |
| 94 | D (85) | n-C₃H₇—H—COO—⬡—⬡—CN | (15) | −3 | 84 | 2.9 |
| 95 | D (70) | n-C₃H₇—H—COO—⬡—⬡—CN | (10) | −12 | 68 | 1.8 |
|  |  | n-C₄H₉—⬡—COO—⬡—CN | (20) |  |  |  |
| 96 | D (80) | n-C₃H₇—H—COO—⬡—⬡—CN | (10) | −6 | 64 | 2.2 |
|  |  | n-C₃H₇—⬡—COO—⬡(Cl)—CN | (10) |  |  |  |
| 97 | D (65) | n-C₃H₇—H—COO—⬡—⬡—CN | (10) | −11 | 66 | 1.6 |

Table 11-continued
| Example No. | Matrix liquid crystal | $N_p$-type liquid crystal and/or homolog of $N_p$-type liquid crystal | | Transition temperature (°C.) C→N | N⇌I | Threshold voltage, $V_{th}$ (25° C.) (V) |
|---|---|---|---|---|---|---|
| | | 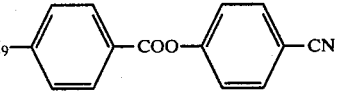 | (20) | | | |
| | | 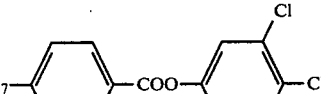 | (5) | | | |
| 98 | D (70) | 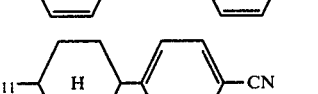 | (30) | −14 | 52.5 | 2.2 |
| 99 | D (70) |  | (30) | −7 | 54 | 2.3 |
| 100 | D (70) | 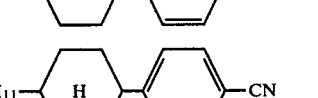 | (20) | −22 | 70 | 2.3 |
| | |  | (10) | | | |
| 101 | D (40) | 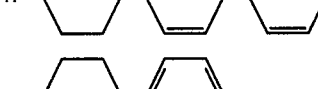 | (20) | −25* | 64 | 1.3 |
| | | 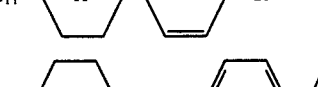 | (10) | | | |
| | |  | (25) | | | |
| | | 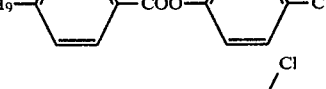 | (5) | | | |
| 102 | D (40) | 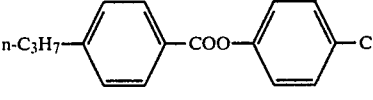 | (20) | −25* | 63 | 1.3 |
| | | 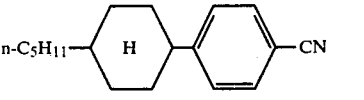 | (10) | | | |
| | | 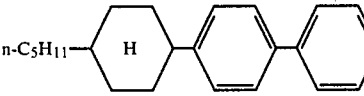 | (5) | | | |
| | | 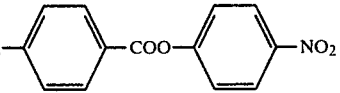 | (25) | | | |

Table 11-continued

| Example No. | Matrix liquid crystal | N_p-type liquid crystal and/or homolog of N_p-type liquid crystal | | Transition temperature (°C.) C→N | N⇌I | Threshold voltage, V_th (25° C.) (V) |
|---|---|---|---|---|---|---|
| 103 | D (60) | n-C$_3$H$_7$–[H]–COO–[Ph]–[Ph]–CN | (10) | −18 | 67 | 1.7 |
|  |  | n-C$_5$H$_{11}$–[Ph]–[Ph]–CN | (30) |  |  |  |
| 104 | D (50) | n-C$_5$H$_{11}$–[H]–[Ph]–CN | (20) | −25* | 63 | 1.4 |
|  |  | n-C$_3$H$_7$–[H]–COO–[Ph]–[Ph]–CN | (5) |  |  |  |
|  |  | n-C$_4$H$_9$–[Ph]–COO–[Ph]–CN | (20) |  |  |  |
|  |  | (CH$_3$)$_2$N–[Ph]–COO–[Ph]–CN | (5) |  |  |  |
| 105 | H (44) | n-C$_5$H$_{11}$–[H]–[Ph]–CN | (25) | −25* | 60.5 | 1.4 |
|  |  | n-C$_4$H$_9$–[Ph]–COO–[Ph]–CN | (25) |  |  |  |
|  |  | n-C$_3$H$_7$–[H]–COO–[Ph]–[Ph]–CN | (6) |  |  |  |
| 106 | E (30) | n-C$_5$H$_{11}$–[H]–[Ph]–CN | (20) | 5 | 60 | 1.2 |
|  |  | n-C$_3$H$_7$–[H]–COO–[Ph]–[Ph]–CN | (10) |  |  |  |
|  |  | n-C$_4$H$_9$–[Ph]–COO–[Ph]–CN | (30) |  |  |  |
|  |  | n-C$_3$H$_7$–[Ph]–COO–[Ph(Cl)]–CN | (10) |  |  |  |
| 107 | I (45) | n-C$_5$H$_{11}$–[H]–[Ph]–CN | (25) | −25* | 64.5 | 1.5 |

Table 11-continued

| Example No. | Matrix liquid crystal | N$_p$-type liquid crystal and/or homolog of N$_p$-type liquid crystal | C →N | N ⇌ I | Threshold voltage, V$_{th}$ (25° C.) (V) |
|---|---|---|---|---|---|
| 108 | D (60) | n-C$_4$H$_9$—〈 〉—COO—〈 〉—CN (24)<br>n-C$_3$H$_7$—〈H〉—COO—〈 〉—〈 〉—CN (6)<br>n-C$_5$H$_{11}$—〈H〉—〈 〉—CN (20)<br>n-C$_5$H$_{11}$—〈 〉—〈 〉—〈 〉—CN (10) | −8 | 62 | 1.6 |
| 109 | D (60) | n-C$_3$H$_7$—〈 〉—COO—〈 〉(Cl)—CN (10)<br>n-C$_5$H$_{11}$—〈H〉—COS—〈 〉—CN (20) | −3 | 57 | 1.7 |
| 110 | J (50) | n-C$_4$H$_9$—〈 〉—COO—〈 〉—CN (20)<br>n-C$_5$H$_{11}$—〈H〉—〈 〉—CN (25) | −25* | 63 | 1.45 |
| 111 | K (50) | n-C$_4$H$_9$—〈 〉—COO—〈 〉—CN (20)<br>n-C$_3$H$_7$—〈 〉—COO—〈 〉(Cl)—CN (5)<br>n-C$_5$H$_{11}$—〈H〉—〈 〉—CN (25) | −25* | 59 | 1.45 |
| 112 | L (50) | n-C$_4$H$_9$—〈 〉—COO—〈 〉—CN (20)<br>n-C$_3$H$_7$—〈 〉—COO—〈 〉(Cl)—CN (5)<br>n-C$_5$H$_{11}$—〈H〉—〈 〉—CN (25) | −25* | 63 | 1.45 |

Table 11-continued

| | Mixed liquid crystalline composition (mole %) | | Transition temperature (°C.) | | Threshold voltage, $V_{th}$ (25° C.) |
|---|---|---|---|---|---|
| Example No. | Matrix liquid crystal | $N_p$-type liquid crystal and/or homolog of $N_p$-type liquid crystal | C→N | N⇌I | (V) |
| | | n-C₄H₉—⟨⟩—COO—⟨⟩—CN  (20) | | | |
| | | n-C₃H₇—⟨⟩—COO—⟨⟩(Cl)—CN  (5) | | | |

The mixed liquid crystals shown in Table 11 have a broadened mesomorphic range over the matrix liquid crystals used, and it is especially noteworthy that the C→N transition temperature shifts to a low temperature side, and the N⇌C transition temperature shifts to a high temperature side. This shows that owing to the presence of the compound of formula (I) as part of the matrix liquid crystal, the individual constituents of the mixed liquid crystal dissolve in each other very well. The mixed liquid crystals shown in Table 11 have a broad mesomorphic range including room temperature, a viscosity at 25° C. of as low as about 35 centipoises, and a threshold voltage of as low as 1 to 3 volts. It is seen therefore that the nematic liquid crystalline compositions of this invention are useful as liquid crystals for FEM cells.

As is clearly understood from the foregoing description, the nematic liquid crystalline compositions of this invention have various superior properties useful for practical applications. Specifically, they can perform a clear display because they are white in color; they have a high reliability and a long service life because they are chemically stable and have resistance to degradation by moisture, light, etc.; they have a broad mesomorphic range including room temperature; they have a fast speed of response because they have a low viscosity; and they can be driven at low voltages because their threshold voltages can be adjusted to low volts.

What we claim is:

1. A trans(equatorial-equatorial)1,4-disubstituted cyclohexane derivative of the general formula

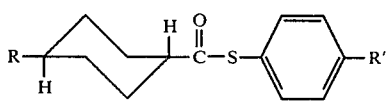

wherein R represents a linear alkyl group containing 3 to 7 carbon atoms and R' represents a linear alkoxy group containing 2 to 5 carbon atoms or a cyano group.

2. A nematic liquid crystalline composition comprising at least two trans(equatorial-equatorial)1,4-disubstituted cyclohexane derivatives, which are nematic liquid crystalline compounds, of the general formula

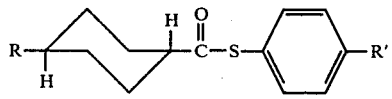

wherein R represents a linear alkyl group containing 3 to 7 carbon atoms, and R' represents a linear alkoxy group containing 2 to 5 carbon atoms or a cyano group.

3. A nematic liquid crystalline composition comprising at least one trans(equatorial-equatorial)1,4-disubstituted cyclohexane derivative, a nematic liquid crystalline compounds, of the general formula

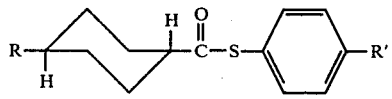

wherein R represents a linear alkyl group containing 3 to 7 carbon atoms, and R' represents a linear alkoxy group containing 2 to 5 carbon atoms or a cyano group, and at least one additional component selected from the group consisting of other nematic liquid crystalline compounds and homologs thereof which are not liquid crystalline.

4. The composition of claim 3 wherein the additional component is a compound of the general formula

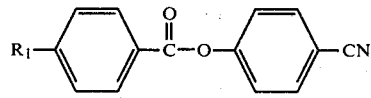

wherein $R_1$ represents n—$C_mH_{2m+1}$—, or n—$C_mH_{2m+1}$—O— in which m is an integer of 1 to 10.

5. The composition of claim 3 wherein the additional component is a compound of the general formula

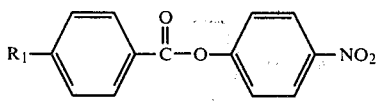

wherein $R_1$ represents n—$C_mH_{2m+1}$—, or n—$C_mH_{2m+1}$—O— in which m is an integer of 1 to 8.

6. The composition of claim 3 wherein the additional component is a compound of the general formula

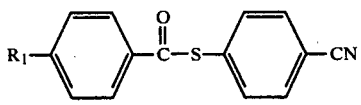

wherein $R_1$ represents n—$C_mH_{2m+1}$— in which m is an integer of 1 to 10.

7. The composition of claim 3 wherein the additional component is a compound of the general formula

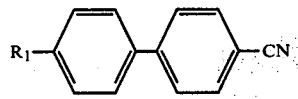

wherein $R_1$ represents n—$C_mH_{2m+1}$—, n—$C_mH_{2m+1}$—O—, or

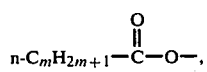

in which m is an integer of 1 to 10.

8. The composition of claim 3 wherein the additional component is a compound of the general formula

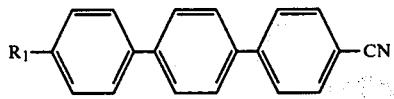

wherein $R_1$ represents n—$C_mH_{2m+1}$— in which m is an integer of 1 to 8.

9. The composition of claim 3 wherein the additional component is a compound of the general formula

wherein $R_1$ represents n—$C_mH_{2m+1}$— or n—$C_mH_{2m+1}$—O— in which m is an integer of 1 to 10.

10. The composition of claim 3 wherein the additional component is a compound of the general formula

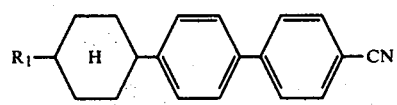

wherein $R_1$ represents n—$C_mH_{2m+1}$— or n—$C_mH_{2m+1}$—O— in which m is an integer of 1 to 1 8.

11. The composition of claim 3 wherein the additional component is a compound of the general formula

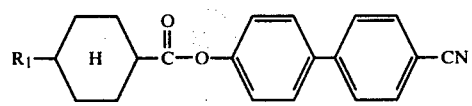

wherein $R_1$ represents n—$C_mH_{2m+1}$— in which m is an integer of 1 to 10.

12. The composition of claim 3 wherein the additional component is a compound of the general formula

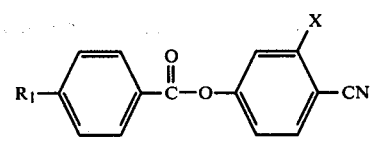

wherein $R_1$ represents n—$C_mH_{2m+1}$— in which m is an integer of 1 to 8, and X represents F, Cl, Br or I.

13. The composition of claim 3 wherein the additional component is a compound of the general formula

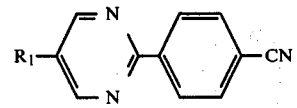

wherein $R_1$ represents n—$C_mH_{2m+1}$ in which m is an integer of 1 to 10.

14. The composition of claim 3 wherein the additional component is a compound of the general formula

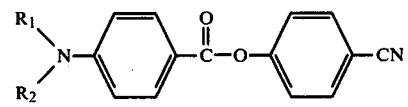

wherein each of $R_1$ and $R_2$ represents n—$C_mH_{2m+1}$— in which m is an integer of 1 to 5.

15. The composition of claim 3 wherein the additional component is a compound of the general formula

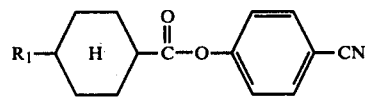

wherein $R_1$ represents n—$C_mH_{2m+1}$— in which m is an integer of 1 to 10.

16. The composition of claim 3 wherein the additional component is a compound of the general formula

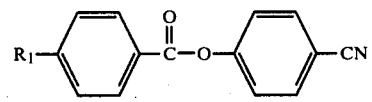

wherein $R_1$ represents n—$C_mH_{2m+1}$— in which m is an integer of 1 to 10.

17. The composition of claim 3 wherein the additional component is a compound of the general formula

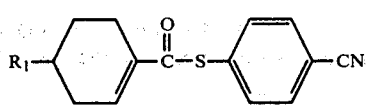

wherein $R_1$ represents n—$C_mH_{2m+1}$— in which m is an integer of 1 to 10.

18. The composition of any one of claims 4 to 17 which consists of 98 to 30 mole% of the trans(equatorial-equatorial) 1,4-disubstituted cyclohexane derivative and 2 to 70 mole% of the additional component.

19. The composition of claim 3 wherein the additional component is a compound of the general formula

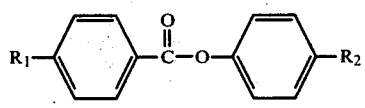

wherein $R_1$ and $R_2$ each represent n—$C_mH_{2m+1}$—, n—$C_mH_{2m+1}$—O—, n-$C_mH_{2m+1}$—$\overset{O}{\underset{\|}{C}}$—O—, n-$C_mH_{2m+1}$—$\overset{O}{\underset{\|}{C}}$—, or n-$C_mH_{2m+1}$—O—$\overset{O}{\underset{\|}{C}}$—O—, in which m is an integer of 1 to 10.

20. The composition of claim 3 wherein the additional component is a compound of the general formula

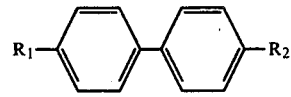

wherein each of $R_1$ and $R_2$ represents n—$C_mH_{2m+1}$—, n—$C_mH_{2m+1}$—O—, or n-$C_mH_{2m\,+\,1}$—$\overset{O}{\underset{\|}{C}}$— in which m is an integer of 1 to 10.

21. The composition of claim 3 wherein the additional component is compound of the general formula

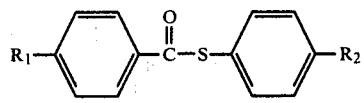

wherein each of $R_1$ and $R_2$ represent n—$C_mH_{2m+1}$ or n—$C_mH_{2m+1}$—O— in which m is an integer of 1 to 10.

22. The composition of claim 3 wherein the additional component is a compound of the general formula

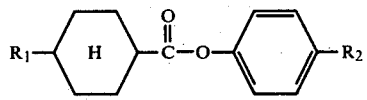

wherein $R_1$ represents n—$C_mH_{2m+1}$—, and $R_2$ represents n—$C_{m'}H_{2m'+1}$—, n—$C_{m'}H_{2m'+1}$—O— or n-$C_{m'}H_{2m'+1}$—$\overset{O}{\underset{\|}{C}}$—, in which m and m' are integers of 1 to 10.

23. The composition of claim 3 wherein the additional component is a compound of the general formula

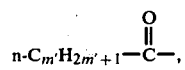

wherein $R_1$ represents n—$C_mH_{2m+1}$— and $R_2$ represents n—$C_{m'}H_{2m'+1}$— or n—$C_{m'}H_{2m'+1}$—O—, in which m and m' are integers of 1 to 10.

24. The composition of claim 3 wherein the additional component is a compound of the general formula

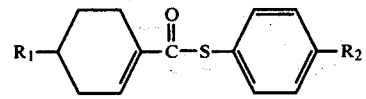

wherein $R_1$ and $R_2$ each represent n—$C_mH_{2m+1}$— or n—$C_mH_{2m+1}$—O— in which m is an integer of 1 to 6.

25. The composition of claim 3 wherein the additional component is a compound of the general formula

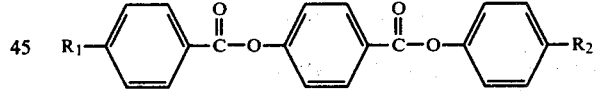

wherein $R_1$ and $R_2$ each represent n—$C_mH_{2m+1}$— or n—$C_mH_{2m+1}$—O—, in which m is an integer of 1 to 8.

* * * * *

UNITED STATES PATENT AND TRADEMARK OFFICE
CERTIFICATE OF CORRECTION

PATENT NO. : 4,202,791
DATED : May 13, 1980
INVENTOR(S) : Sato et al.

It is certified that error appears in the above—identified patent and that said Letters Patent is hereby corrected as shown below:

On the title page the title should read

-- Novel Nematic Liquid Crystalline Materials --.

Signed and Sealed this

Second Day of December 1980

[SEAL]

Attest:

SIDNEY A. DIAMOND

Attesting Officer

Commissioner of Patents and Trademarks